United States Patent [19]

Kazan et al.

[11] 4,260,815

[45] Apr. 7, 1981

[54] PROCESS FOR PREPARING A SOLUTION OF DL-MANDELIC ACID

[75] Inventors: John Kazan, Bridgewater; Chen S. Yu, Middlesex, both of N.J.

[73] Assignee: American Cyanamid Company, Stamford, Conn.

[21] Appl. No.: 83,183

[22] Filed: Oct. 9, 1979

[51] Int. Cl.³ ............................................. C07B 20/00
[52] U.S. Cl. ................................. 562/401; 562/470
[58] Field of Search ............................... 562/401, 470

[56] References Cited

U.S. PATENT DOCUMENTS 3,686,183  8/1972  Dyson ................................ 562/401

FOREIGN PATENT DOCUMENTS 2415402  10/1974  Fed. Rep. of Germany .
2436682  2/1975  Fed. Rep. of Germany .
2733425  1/1979  Fed. Rep. of Germany .

OTHER PUBLICATIONS

Stoll et al., Helv. Chim. Acta 26, p. 941, (1943).

*Primary Examiner*—Natalie Trousof
*Assistant Examiner*—Vera C. Clarke
*Attorney, Agent, or Firm*—Jack W. Richards

[57] ABSTRACT

A process for preparing a solution of DL-mandelic acid is disclosed. The process consists essentially of heating a solution consisting essentially of an optically active 2-amino-1-butanol mandelate and an alkalizing agent, with or without an alcohol solvent; neutralizing the resulting solution with a mineral acid or a mineral acid salt to precipitate an alkali or alkaline earth metal salt; separating the metal salt; and recovering the solution of DL-mandelic acid.

4 Claims, No Drawings

PROCESS FOR PREPARING A SOLUTION OF DL-MANDELIC ACID

BACKGROUND AND SUMMARY OF THE INVENTION

This invention relates to a process for preparing a solution of DL-mandelic acid.

More particularly, it relates to a process wherein higher productivity and improved economics are achieved by the use of more concentrated reaction mixtures, more simplified processing, and very high utilization of key raw materials.

The Applicants are not aware of any prior art references which, in their respective judgments, as persons skilled in the resolution and racemization art, anticipate or render obvious this invention. The publications cited herein may be of assistance in developing the background of this invention and establishing the state of the prior art. The publications are incorporated by reference.

The use of optically active amines to resolve racemic mixtures of carboxylic acids, such as DL-mandelic acid, is well-known. The use of (−)-2-amino-1-butanol to resolve DL-mandelic acid is disclosed by Riedel De Haen AG, West German DT2733-425.

The present invention arose out of research for a more satisfactory process for the resolution of DL-mandelic acid. This research resulted in the discovery of a process for preparing DL-mandelic acid, with or without a lower aliphatic alcohol solvent, utilizing essentially an optically active 2-amino-1-butanol mandelate and an alkalizing agent.

The utility of one of the products of the process of the present invention, D-(−)-mandelic acid, and its derivatives, is known. See, e.g., Germ. Offen. No. 2,415,402 and Germ. Offen. 2,436,686, and English language abstract of which is disclosed in Chem. Abs. 82, 31343m (1975) and Chem. Abs. 83, 10556p (1976), respectively.

In accordance with the present invention, there is provided a process for preparing a solution of DL-mandelic acid. The known process for resolving DL-mandelic acid comprises: (a) reacting DL-mandelic acid with optically active 2-amino-1-butanol in water, in a lower aliphatic alcohol or in a mixture thereof, at a temperature of about 20° to 60° C., to form an optically active mandelate salt represented by formula (I)

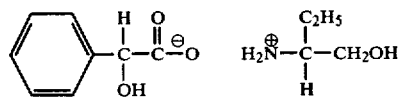

(b) cooling and recovering the optically active mandelate salt; (c) mixing the mandelate salt with water, and distilling off any residual alcohol at a temperature of about 50° to 90° C.; (d) acidifying the alcohol-free mixture with a mineral acid; and (e) cooling and recovering optically active mandelic acid. An improvement in the process comprises:

(1) recycling the mother liquor of step (b) into step (a) until the mother liquor becomes saturated with the diasteromeric isomer of the mandelate salt;
(2) (i) heating the mother liquor with an alkalizing agent to obtain a racemic solution; or
  (ii) heating a mixture consisting essentially of an optically active 2-amino-1-butanol, an optically active mandelic acid, and an alkalizing agent, substantially in the absence of any other solvent, containing DL-mandelic acid and an optically active 2-amino-1-butanol.
(3) neutralizing the racemic solution with a mineral acid, a mineral acid salt of optically active 2-amino-1-butanol, or a mineral acid salt of optically active 2-amino-1-butanol and mandelic acid, in a lower aliphatic alcohol, to precipitate an alkali or alkaline earth metal salt;
(4) separating the metal salt;
(5) recycling the mother liquor of step (4) into step (a); and
(6) recycling the mother liquor of step (e) into step (c) until the mother liquor becomes saturated with a mineral acid salt of optically active 2-amino-1-butanol and mandelic acid.

In an alternative embodiment, the improvement in the process comprises the additional steps of:

(7) heating the saturated mother liquor of step (6) to remove water;
(8) dissolving the residue of step (7) in a lower aliphatic alcohol; and
(9) recycling the solution of step (8) into step (3).

In an alternative embodiment to the improvement, and to the preferred embodiment of the improvement, the optically active 2-amino-1-butanol in step (a) is (−)-2-amino-1-butanol; the alcohol in steps (a) and (3) and in step (8) of the preferred embodiment is methanol; the alkalizing agent in step (2) is potassium hydroxide; the mineral acid salt in step (3) is (−)-2-amino-1-butanol hydrochloride; and the mineral acid salt and mandelic acid in step (6) are (−)-2-amino-1-butanol hydrochloride and D-(−)-mandelic acid. Preferably, the racemic solution in step (3) is neutralized with (−)-2-amino-1-butanol hydrochloride and optically active mandelic acid. More preferably, the mandelic acid is D-(−)-mandelic acid.

In another alternative embodiment to the improvement, and to the preferred embodiment of the improvement, the optically active 2-amino-1-butanol in step (a) is (+)-2-amino-1-butanol; the alcohol in steps (a) and (3) and in step (8) of the preferred embodiment is methanol; the alkalizing agent in step (2) is potassium hydroxide; the mineral acid salt in step (3) is (+)-2-amino-1-butanol hydrochloride; and the mineral acid salt and mandelic acid in step (6) are (+)-2-amino-1-butanol hydrochloride and L-(+)-mandelic acid. Preferably, the racemic solution in step (3) is neutralized with (+)-2-amino-1-butanol hydrochloride and an optically active mandelic acid. More preferably, the mandelic acid is L-(+)-mandelic acid.

The improved process of the present invention for the resolution of DL-mandelic acid is more productive than the processes of the prior art and obviates the preparation of optically active 2-benzylamino-1-butanols.

In accordance with the present invention, there is also provided a process for preparing a solution of mandelic acid. This process consists essentially of:

(a) heating an optically active 2-amino-1-butanol mandelate and an alkalizing agent in a lower aliphatic alcohol or alcohol mixture, or in a lower aliphatic alcohol and water, said alcohol water mixture containing up to about 20% by weight of water, until racemization is essentially complete;
(b) neutralizing the resulting solution with a mineral acid or a mineral acid salt of 2-amino-1-butanol and mandelic acid in the lower aliphatic alcohol or alcohol mixture to precipitate an alkali or alkaline earth metal salt;

(c) separating the metal salt; and (d) recovering the resulting solution of DL-mandelic acid.

By "lower aliphatic" is meant a straight or branched open-chain radical containing one to about six carbon atoms. A lower alkyl alcohol is preferred. By "lower alkyl" is meant a saturated straight or branched open-chain radical containing one to about six carbon atoms.

In one embodiment, the alkalizing agent is potassium hydroxide, the lower alcohol is methanol and the mineral acid is hydrogen chloride.

In another embodiment, the alkalizing agent is potassium hydroxide, the lower alcohol is methanol and the mineral acid salt and mandelic acid are (−)-2-amino-1-butanol hydrochloride and D-(−)-mandelic acid.

In yet another embodiment, the alkalizing agent is potassium hydroxide, the lower alcohol is methanol and the mineral acid salt and mandelic acid is (+)-2-amino-1-butanol hydrochloride and L-(+)-mandelic acid.

The process of the present invention for the preparation of a solution of DL-mandelic acid is unique in that the racemization of the optically active mandelic acid is carried out in the presence of an optically active 2-amino-1-butanol that is resistant to racemization under the conditions employed. This results in increased productivity because the separation of the optically active 2-amino-1-butanol and the other optical isomer of mandelic acid is avoided. Also, the optically active 2-amino-1-butanol and the other optical isomer of mandelic acid are essentially 100% recycled.

DESCRIPTION OF PREFERRED EMBODIMENTS

The optically active 2-amino-1-butanols used in the resolution process of the present invention are well-known. The preparation of dextrorotatory 2-amino-1-butanol is described by Halmos et al. in U.S. Pat. No. 3,553,257. The preparation of levorotatory 2-amino-1-butanol is described by Stoll et al., Helv. Chim. Acta 26, pg 941 (1943).

The improved resolution process of this invention may be divided into the following stages:

(1) FORMATION AND ISOLATION OF MANDELATE SALT

A solution containing about 20–60%, preferably about 30–50%, by weight of DL-mandelic acid in a suitable solvent, such as water, methanol, ethanol, n-propanol, isopropanol, sec-butanol, and the like, or mixtures thereof, is stirred at ambient to moderately elevated temperatures, preferably about 20°–30° C., with the optically active 2-amino-1-butanol using about 0.5 to 3, preferably about 1 to 2, molecular proportions of the 2amino-1-butanol per molecular proportion of DL-mandelic acid to form the optically active mandelate salt of formula (I). The reaction mixture is then cooled to about −10° to 15° C., preferably about 0° to 5° C. to crystallize the optically active mandelate salt which is recovered by conventional methods to obtain either (−)-2-amino-1-butanol D-(−)-mandelate, or (+)-2-amino-1-butanol L-(+)-mandelate.

The preferred solvent is methanol and the preferred optically active 2-amino-1-butanol is the levorotatory isomer. The mother liquor from the isolation of the mandelate salt is then recycled several times in other resolution reactions until it is saturated with the diastereomer of the isolated mandelate salt.

The overall yield of the recovered crude mandelate salt is about 93% of theoretical after recycling the mother liquor twice. Optionally, the crude mandelate salt may be further purified by recrystallization before proceeding further.

(2) RACEMIZATION

As previously mentioned, the mother liquor obtained by separating the desired mandelate salt can be recycled several times in subsequent resolution reactions. However, when the mother liquor becomes essentially saturated with a mixture of diastereomers, which is about 94% by weight of the undesired diastereomer and about 6% by weight of the desired diastereomer, a racemization is carried out. This is effected by refluxing, or by heating under pressure at an elevated temperature, the saturated mother liquor containing an optically active 2-amino-1-butanol mandelate salt, preferably (−)-2-amino-1-butanol L-(+)-mandelate, with an alkalizing agent, such as potassium hydroxide, sodium hydroxide, calcium hydroxide, and the like, preferably potassium hydroxide, in a lower alcohol, a mixture of lower alcohols, or a mixture of a lower alcohol and water, using about 1—2, preferably about 1.1–1.3, molecular proportions of the alkalizing agent per molecular proportion of the mandelate salt. Suitable lower alcohols include methanol, ethanol, n-propanol, isopropanol, sec-butanol, and the like. The preferred lower alcohol is methanol. When the racemization is completed, the solution is neutralized by adding a mineral acid, such as hydrogen chloride, hydrochloric acid, sulfuric acid, and the like, an alcohol solution of a mineral acid salt of an optically active 2-amino-1-butanol, or an alcohol solution of a mineral acid salt of an optically active 2-amino-1-butanol and a mandelic acid, preferably a solution of (−)-2-amino-1-butanol hydrochloride and D(−)-mandelic acid in methanol, to precipitate an alkali metal, or alkaline earth metal, salt. Separation of the precipitate affords a solution containing essentially DL-mandelic acid and an optically active 2-amino-1-butanol, preferably (−)-2-amino-1-butanol, which can be recycled in a subsequent resolution reaction.

Optionally, and preferably, the mother liquor, after the addition of the alkalizing agent, as previously described, is distilled to remove essentially all of the solvent. The distillation heel, now a mixture consisting essentially of an optically active 2-amino-1-butanol, preferably (−)-2-amino-1-butanol, an optically active mandelic acid, preferably L-(+)-mandelic acid, the alkalizing agent, preferably potassium hydroxide, and a few percent of residual water, is refluxed under atmospheric pressure at 110°–135° C. until racemization is completed. When racemization is completed, the solution is processed as described previously to provide a solution of DL-mandelic acid and (−)-2-amino-1-butanol for recycle in a subsequent resolution reaction.

(3) ISOLATION OF OPTICALLY ACTIVE MANDELIC ACID

The optically active mandelate salt obtained in (1) is dissolved in water and the solution is heated at about 40°–70° C., preferably at about 50°–65° C., to distil off any residual lower alcohol. The alcohol-free solution is then acidified to about pH 0–4.0, preferably about 0.5–1.2, to liberate the optically active mandelic acid.

Suitable acids which may be used for this purpose include hydrochloric, sulfuric, phosphoric acid, and the like. The preferred acid is hydrochloric acid. The acidified solution is then cooled to about −10° to 15° C., preferably about −5° to 5° C., to crystallize out the optically active mandelic acid which is recovered by conventional means to obtain either D-(−)- or L-(+)-mandelic acid.

The overall yield of D-(−)- or L-(+)-mandelic acid is about 75–85% of theoretical. Optionally, the acid may be further purified by recrystallization from a suitable solvent, such as water.

Optionally, the mother liquor obtained by the recovery of the crude optically active mandelic acid, consisting essentially of an aqueous solution of an acid salt of an optically active 2-amino-1-butanol, preferably (−)-2-amino-1-butanol hydrochloride, and the corresponding optically active mandelic acid, preferably D-(−)-mandelic acid, is heated to remove the water by distillation. The residue is then dissolved in a lower alcohol, preferably methanol, to obtain a solution of the acid salt of the optically active 2-amino-1-butanol and the optically active mandelic acid, preferably a solution of (−)-2-amino-1-butanol and D-(−)-mandelic acid in methanol, which is utilized as a neutralizing agent in the racemization stage.

The racemization process of the present invention is carried out essentially as described in the sections under Racemization and Isolation, previously described, except that instead of starting with an optically active mandelate salt one can also start with an optically active mandelic acid. The feature of the racemization process is the fact that the resolving agent, optically active 2-amino-1-butanol, is not separated from the mandelic acid, or mandelate salt, before carrying out the racemization.

The following examples further illustrate the invention. All parts and percentages are by weight unless otherwise specified. All ranges expressed are inclusive of both numbers.

Unless otherwise indicated, optical rotations were measured by dissolving 2.0 or 6.0 grams of the compound in 100 mls of water and determining the specific rotation of the plane of a sodium D line at 25° C. The specific rotation is indicated by a bracket. Unbracketed rotations indicate observed rotations of the solution "as is", that is, not as a 100% pure compound in solution.

EXAMPLE 1

(A) DL-Mandelic acid (1526 grams "as is"—99.7% pure; 10.0 moles) is dissolved in methanol (2250 mls) and (−)-2-amino-1-butanol (900 grams "as is"— 90.0% pure; 10.0 moles) is added slowly to the solution at 45°–50° C. The solution is then cooled to 38°–40° C. seeded with (−)-2-amino-1-butanol D-(−)-mandelate salt, and further cooled to 0°–5° C. over about 6 hours to obtain a crystalline precipitate. The crystals are isolated in two equal portions and each portion of wet cake is washed three times with cold (0°–5° C.) methanol (100 mls). The resulting wet cakes are combined to obtain a wet cake containing 1066 grams of (−)-2-amino-1-butanol D-(−)-mandelate (88.5% of theoretical; m.p. 128°–131° C.; $[\alpha]_D^{25°} = -77.1°$ (C=6, H$_2$O)).

(B) The mother liquor and methanol washes obtained from resolution (A) are combined and warmed to 45°–50° C. To the solution are added DL-mandelic acid (1369 grams "as is" 99.7% pure; 8.97 moles), and (−)-2-amino-1-butanol (793 grams "as is" 90.0% pure; 8.81 moles), and the resulting solution is cooled to 0°–5° C. in about 5.5 hours to obtain a crystalline precipitate. The crystals are isolated in two equal portions and each portion of wet cake is washed three times with cold (0°–5° C.) methanol (110 mls). The resulting wet cakes are combined to obtain a wet cake which contains 1083 grams of (−)-2-amino-1-butanol D-(−)-mandelate salt 89.9% of theoretical; m.p. 126°–130° C.; $[\alpha]_D^{25°} = -73.7°$ (C=6, H$_2$O).

The combined yield of A and B is 93.6% of theoretical.

(C) To a portion (1100 mls out of a total of 4800 mls) of the mother liquor plus methanol wash liquor obtained from resolution B, containing about 2.4 moles of a mixture of diastereomers, consisting of about 2.25 moles of (−)-2-amino-1-butanol L-(+)-mandelate and about 0.15 mole of (−)-2-amino-1-butanol D-(−)-mandelate, is added 180 grams of potassium hydroxide (88.8% real; 2.85 moles) to obtain a solution having an initial $\alpha_D^{25°}$ C of +24.7° ("as is", 10 cm cell). The solution is then heated at 115°–116° C. under pressure (40 psi) for 4 hours to obtain a mandelic acid solution having an $\alpha_D^{25°}$ C. of −3.0° ("as is", 10 cm cell). The resulting solution is essentially racemized, the negative rotation being due to the presence of the (−)-2-amino-1-butanol.

The racemized solution is neutralized with 98% sulfuric acid (147 grams; 1.47 moles) and the resulting slurry of potassium sulfate is treated with a filter aid (59 grams of Hyflo ®Super-Cel; Johns-Manville Sales Corp.), diluted with methanol (340 mls), and filtered while hot (50°–55° C.). The filter cake is washed with warm (40°–45° C.) methanol (170 mls) and the wash liquor is combined with the mother liquor. The combined solution, containing equimolecular amounts of DL-mandelic acid, and (−)-2-amino-1-butanol, is concentrated by distillation to a volume of 1000 mls. The resulting solution is cooled to 35°–40° C., seeded with (−)-2-amino-1-butanol D-(−)-mandelate salt, and further cooled to 0°–5° C. over 3–4 hours to obtain crystals of (−)-2-amino-1-butanol D-(−)-mandelate salt. The crystals are isolated by filtration, washed twice with cold (0°–5° C.) methanol (100 mls), and dried at 60° C. to obtain (−)-2-amino-1-butanol D-(−)-mandelate (257.4 grams; 89% of theoretical; m.p. 127°–131° C.; $[\alpha]_D^{25°} = -75°$ (C=6, H$_2$O).

(D) A portion of the (−)-2-amino-1-butanol D-(−)-mandelate wet cake (155 grams "as is" −90.3% pure; 0.58 mole) from resolution A is dissolved in water (125 mls) at 50°–55° C. and the resulting solution is distilled under vacuum to remove 48.5 mls of methanol and water. The concentrated solution is treated with 37% hydrochloric acid (60 mls) and the acidified solution is cooled to −5° C. over about 5 hours to crystallize D-(−)-mandelic acid from the solution. The crystals are isolated by filtration, washed twice with ice cold (0°–5° C.) water (20 mls), twice with hexane (20 mls), and dried at 60° C. to obtain 64.1 grams of D-(−)-mandelic acid (72.6% of theoretical; m.p. 131°–133° C.; $[\alpha]_D^{25} = -154.1°$ (C=2, H$_2$O)).

(E) A portion of the (−)-2-amino-1butanol D-(−)-mandelate wet cake 155 grams "as is" −90.3% pure; 0.58 mole) from resolution A is dissolved in the mother liquor plus water washes from (D) at 50°–55° C. and the solution is distilled under vacuum to remove 41 mls of methanol and water. The concentrated solution is then treated with 37% hydrochloric acid (60 mls) and processed as described in (D) to obtain 77 grams of D-(−)- mandelic acid (87.4% of theoretical; m.p. 130°–132° C.; $[\alpha]_D^{25} = -152.9°$ (C=2, H$_2$O)).

(F) The procedure of (E) is followed in every detail except that the mother liquor plus water washes from (E) is used instead of from (D). There is obtained 66.9 grams of D-(−)-mandelic acid (75.7% of theoretical; mp. 130.5°–131.5° C.; $[\alpha]_D^{25} = -152.4°$ (C=2, H$_2$O)).

The above example illustrates recycling of the mother liquor plus wash liquor in the resolution step (A and B), the racemization step (C), and recycling (E and F) of the mother liquor plus wash liquor in the isolation step (D).

EXAMPLE 2

The methanol-wet (−)-2-amino-1-butanol D-(−)-mandelate obtained in Example 1 B (80.7 grams; 70 grams dry weight) is dissolved in water (100 mls) and the solution is heated to remove 12 mls of methanol-containing distillate. The remaining solution is acidified by adding 98% sulfuric acid (14.3 grams) over a period of about 5 minutes. The acidified solution is seeded with D-(−)-mandelic acid at about 32° C. and cooled to 0° C. over a period of about 4 hours. The resulting crystalline precipitate is isolated by filtration and washed successively with ice cold (0°–5° C.) water (2×10 mls) and hexane (2×10 mls). After drying at 60° C., there is obtained D-(−)-mandelic acid (30.3 grams; 68.5% of theoretical; m.p. 131°–132.5° C.; $[\alpha]_D^{25} = -152.8$ (C=2, H$_2$O)).

The above example illustrates the use of 98% sulfuric acid as the acidifying agent to form D-(−)-mandelic acid.

EXAMPLE 3

In the manner described in Example 1, substituting 10.0 moles of d-2-amino-1-butanol for the (−)-2-amino-1-butanol, (+)-2-amino-1-butanol L-(+)-mandelate is obtained and L-(+)- mandelic acid is obtained therefrom.

EXAMPLE 4

A portion (1200 mls) of the mother liquor plus methanol wash liquor (4800 mls) obtained from resolution B of Example 1 is racemized, as described in Example 1, and concentrated to remove 660 mls of distillate. A solution of (−)-2-amino -1-butanol hydrochloride (2.73 moles) in methanol, containing 2.87% water, is added to the residue while stirring and allowing the temperature to rise. The resulting mixture is heated to 55°–60° C., diluted with 200 mls of methanol, and stirred at 50°–60° C. for one hour. the slurry is filtered at 50°–55° C. to separate the potassium chloride precipitate and the wet cake is rinsed with hot methanol (3×50 mls).

The combined filtrate plus washings (1225 mls) is heated to 52° C., cooled to 45° C., and seeded with (−)-2-amino-1-butanol D-(−)-mandelate salt. The seeded solution is cooled to room temperature over about 5 hours and then cooled to 0°–5° C. over about one hour to obtain crystals of (−)-2-amino-1-butanol D-(−)-mandelate salt. The crystals are isolated by filtration after stirring at 0°–5° C. for 0.5 hour, washed twice with cold (0°–5° C.) methanol (75 mls) and dried to obtain (−)-2-amino-1-butanol D-(−)-mandelate (202.8 grams; 70% of theoretical); m.p. 128°–130° C.; $[\alpha]_D^{25} = 73.2$ (C=6, H$_2$O)).

The above example illustrates the use of (−)-2-amino-1-butanol hydrochloride as the neutralizing agent after the racemization is completed.

EXAMPLE 5

In the manner described in Example 1, substituting 10.0 moles of (+)-2-amino-1-butanol for the (+)-2-amino-1-butanol and separating (+)-2-amino-1-butanol L-(+)-mandelate, the mother liquor is recycled two more times in resolution reactions with DL-mandelic acid (1526 grams "as is" —99.7% pure; 10.0 moles). After recycling the mother liquor twice, and separating the (+)-2-amino-1-butanol L-(+)-mandelate salt, the mother liqor is distilled to recover about 80–90% of the methanol for recycling. The residue is diluted with water and distilled under vacuum to remove any residual methanol. The aqueous solution is then acidified with hydrochloric acid to precipitate D-(−)-mandelic acid which is isolated therefrom by filtration.

The above example illustrates a process whereby D-(−)-mandelic acid is obtained from DL-mandelic acid by separating the L-(+)-mandelic acid as the salt of (+)-2-amino-1-butanol and recovering the D-(−)-mandelic acid from the mother liquor.

We claim:

1. A process for preparing a solution of DL-mandelic acid consisting essentially of:
   (a) heating optically active 2-amino-1-butanol mandelate and an alkalizing agent in a lower aliphatic alcohol or alcohol mixture, or in a lower aliphatic alcohol and water, until racemization is essentially complete;
   (b) neutralizing the resulting solution with a mineral acid or a mineral acid salt of 2-amino-1-butanol and mandelic acid in said lower aliphatic alcohol or alcohol mixture to precipitate an alkali or alkaline earth metal salt;
   (c) separating said metal salt; and
   (d) recovering the resulting DL-mandelic acid racemic solution.

2. The process of claim 1 wherein said alkalizing agent is potassium hydroxide, said lower alcohol is methanol and said mineral acid is hydrogen chloride.

3. The process of claim 1 wherein said alkalizing agent is potassium hydroxide, said lower alcohol is methanol and said mineral acid salt and mandelic acid is (−)-2-amino-1-butanol hydrochloride and D-(−)mandelic acid.

4. The process of claim 1 wherein said alkalizing agent is potassium hydroxide, said lower alcohol is methanol and said mineral acid salt and mandelic acid is (+)-2-amino-1-butanol hydrochloride and L-(+)-mandelic acid.

* * * * *